(12) United States Patent
Cohen et al.

(10) Patent No.: US 12,064,282 B2
(45) Date of Patent: Aug. 20, 2024

(54) AUSCULTATION DEVICE FOR DETERMINING AN OPTIMAL LOCATION FOR CARDIORESPIRATORY AUSCULTATION

(71) Applicant: AliveCor, Inc., Mountain View, CA (US)

(72) Inventors: Sean Cohen, Mountain View, CA (US); Ahmad N. Saleh, San Jose, CA (US)

(73) Assignee: ALIVECOR, INC., Mountain View, CA (US)

( * ) Notice: Subject to any disclaimer, the term of this patent is extended or adjusted under 35 U.S.C. 154(b) by 489 days.

(21) Appl. No.: 17/377,216

(22) Filed: Jul. 15, 2021

(65) Prior Publication Data

US 2023/0015506 A1    Jan. 19, 2023

(51) Int. Cl.
*A61B 5/28* (2021.01)
*A61B 5/346* (2021.01)
*A61B 7/00* (2006.01)

(52) U.S. Cl.
CPC .............. *A61B 7/003* (2013.01); *A61B 5/28* (2021.01); *A61B 5/346* (2021.01); *A61B 2562/0204* (2013.01)

(58) Field of Classification Search
CPC . A61B 2562/0204; A61B 5/1102; A61B 5/28; A61B 5/346; A61B 5/349; A61B 5/486; A61B 7/003; A61B 7/04
See application file for complete search history.

(56) References Cited

U.S. PATENT DOCUMENTS

2004/0267148 A1* 12/2004 Arand ................. A61B 5/352
                                                          600/513
2008/0234594 A1*  9/2008 Brooks ................... A61B 7/04
                                                          600/513

* cited by examiner

*Primary Examiner* — George Manuel
(74) *Attorney, Agent, or Firm* — WOMBLE BOND DICKINSON (US) LLP (57) ABSTRACT

Embodiments of the present disclosure relate to determining an optimal location on the body of a person where heart sounds may be optimally heard. The optimal location may be determined at a time prior to the attempted auscultation and ECG data corresponding to the optimal location may be stored in a memory of an auscultation device. Subsequently, when a e.g., physician wishes to listen to the heart sounds of the person, the physician may place the auscultation device at a first location on the patient. The auscultation device may periodically perform an ECG at a current location and use the ECG data at the current location and the ECG data at the optimal location to determine and provide guidance to the physician regarding a direction in which the auscultation device should be moved in order to reach the optimal location.

20 Claims, 9 Drawing Sheets

AUSCULTATION DEVICE FOR DETERMINING AN OPTIMAL LOCATION FOR CARDIORESPIRATORY AUSCULTATION

TECHNICAL FIELD

Aspects of the present disclosure relate to devices for listening to sounds corresponding to the cardiorespiratory activity of a person (referred to as auscultation), and in particular to determining the optimal location on the body of a person to perform auscultation.

BACKGROUND

Cardiorespiratory sounds (referred to herein as heart sounds) may refer to the noises generated by the beating of the heart and the resultant flow of blood through it. For example, some heart sounds may correspond to the turbulence created when heart valves close. In cardiorespiratory auscultation, a person (e.g., physician) may use a stethoscope to listen for these unique and distinct sounds that provide important auditory data regarding the condition of the heart. It is important for a physician to listen to these heart sounds to analyze the heart functioning and heart health of a patient. In healthy adults, there are two normal heart sounds that occur in sequence with each heartbeat. These may be referred to as the first heart sound (S1) and second heart sound (S2) respectively, and may be produced by the closing of the atrioventricular valves and semilunar valves, respectively. In addition to these normal sounds, a variety of other sounds may be present including heart murmurs, adventitious sounds, and gallop rhythms S3 (often referred to as the protodiastolic gallop) and S4 (often referred to as the presystolic gallop).

The heart sounds S1-S4 can provide important auditory data regarding the condition of the heart. For example, whether certain heart sounds S1-S4 are heard or not, and in some cases where in a sequence of heart sounds they are heard may be an indication to a physician of signs that a patient is suffering from a heart condition such as a failing or hypertrophic left ventricle (indicating systemic hypertension), severe valvular aortic stenosis, hypertrophic cardiomyopathy, or congestive heart failure, for example.

BRIEF DESCRIPTION OF THE DRAWINGS

The described embodiments and the advantages thereof may best be understood by reference to the following description taken in conjunction with the accompanying drawings. These drawings in no way limit any changes in form and detail that may be made to the described embodiments by one skilled in the art without departing from the spirit and scope of the described embodiments.

DETAILED DESCRIPTION

Because numerous heart conditions can potentially be detected by listening for heart sounds, hearing these heart sounds clearly and accurately is of critical importance in diagnosing patients with heart conditions. Each heart sound may have different characteristics. For example, certain heart sounds have different pitch, while other heart sounds are heard in rapid succession with preceding and/or following heart sounds. For example, the S4 sound may occur just after atrial contraction at the end of diastole and immediately before the S1 sound. In another example, the S3 sound occurs at the beginning of diastole after the S2 sound and is lower in pitch than either the S1 or S2 sounds, as the S3 sound is not of valvular origin.

However, heart sounds are not heard equally well across the body of a person, and some locations may provide more accurate and clear hearing of the heart sounds than others. In addition, the location on the body of a person where these heart sounds may be heard optimally may be different from person to person, and thus physicians may often be required to approximate the location where heart sounds can be optimally heard. This person to person variances, combined with the variances in pitch and timing of different heart sounds can lead to a physician hearing the heart sounds sub-optimally, and potentially missing indicators of heart conditions as a result. Because of this, it is critically important to determine the location on the body of the patient where the heart sounds may be heard optimally.

The present disclosure addresses the above-noted and other concerns by providing apparatuses and methods to allow anyone to determine a location on the body of a person where heart sounds may be optimally heard (referred to herein as the optimal location). In one embodiment, an apparatus for providing guidance to the location on the body of a person where heart sounds may be optimally heard is provided. The apparatus may comprise a housing, which may comprise an acoustic transducer to detect a set of heart sounds when the housing is placed on a body of a person, a set of electrodes to measure cardiac electrical activity of the person, a memory to store target ECG parameters, and a processing device, operatively coupled to the memory. The target ECG parameters may correspond to an electrocardiogram (ECG) taken at the (previously determined) optimal location on the body of the person where the heart sounds are optimally detected by the acoustic transducer. The processing device may perform, using the set of electrodes, a first ECG of the person when the housing is placed at a first location on the body of the person and determine first ECG parameters of the person based on the first ECG. The processing device may then determine a direction of the optimal location based on the first ECG parameters and the target ECG parameters, and provide an indication of a direction in which the housing is to be moved in order to reach the optimal location.

Figure 1A:
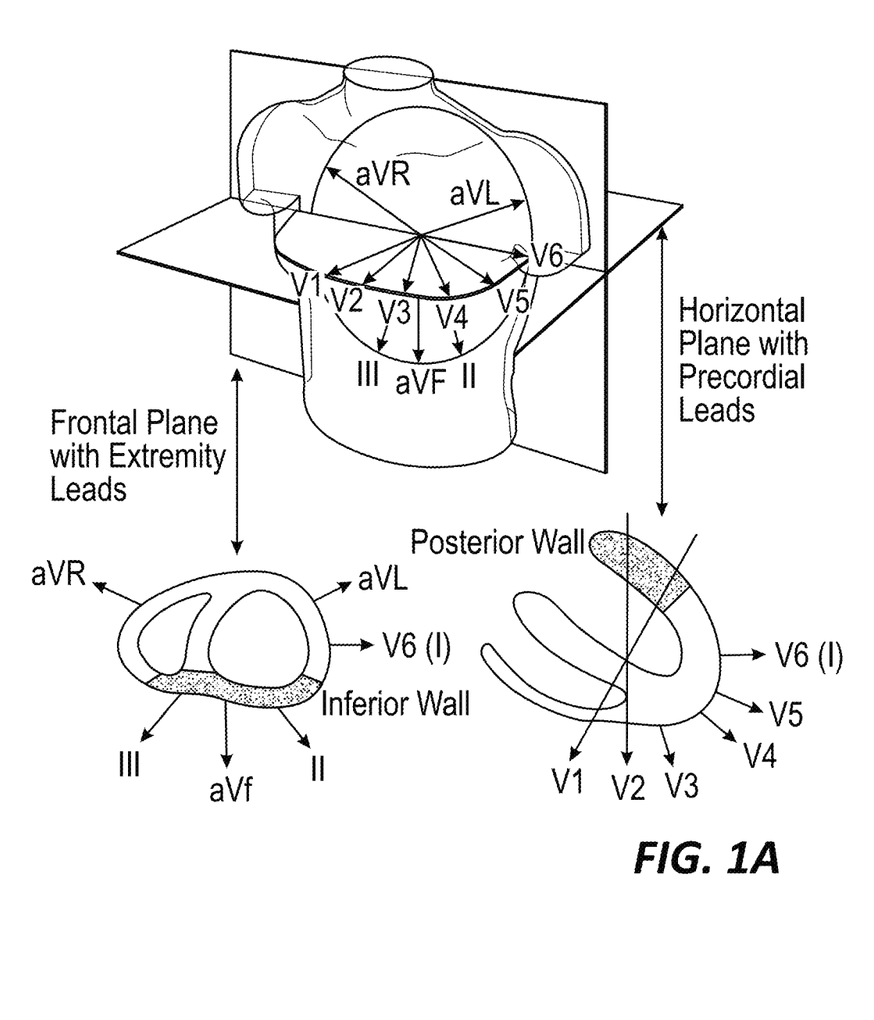
FIG. 1A illustrates a 12 lead set represented on a hexaxial system, in accordance with some embodiments of the present disclosure.

An ECG provides a number of ECG waveforms that represent the electrical activity of a person's heart. An ECG monitoring device may comprise a set of electrodes for recording the ECG waveforms (also referred to herein as "taking an ECG") of the patient's heart. The set of electrodes may be placed on the skin of the patient in multiple locations and the electrical signal (ECG waveform) recorded between each electrode pair in the set of electrodes may be referred to as a lead. Varying numbers of leads can be used take an ECG, and different numbers and combinations of electrodes can be used to form the various leads. Example numbers of leads used for taking ECGs are 3, 5, and 12 leads. FIG. 1A illustrates a 12 lead set comprising the I, II, III, aVR, aVL, aVF, V1, V2, V3, V4, V5, and V6 leads, all represented on a hexaxial system.

The ECG waveforms (each one corresponding to the electrical signal measured by a lead used to take the ECG) recorded by the ECG monitoring device may comprise data corresponding to the electrical activity of the person's heart. A typical heartbeat may include several variations of electrical potential, which may be classified into waves and complexes, including a P wave, a QRS complex, a T wave, and a U wave among others, as is known in the art. Stated differently, each ECG waveform may include a P wave, a QRS complex, a T wave, and a U wave among others, as is known in the art. The shape and duration of these waves may be related to various characteristics of the person's heart such as the size of the person's atrium (e.g., indicating atrial enlargement) and can be a first source of heartbeat characteristics unique to a person. The ECG waveforms may be analyzed (typically after standard filtering and "cleaning" of the signals) for various indicators that are useful in detecting cardiac events or status, such as cardiac arrhythmia detection and characterization. Such indicators may include ECG waveform amplitude and morphology (e.g., QRS complex amplitude and morphology), R wave-ST segment and T wave amplitude analysis, and heart rate variability (HRV), for example.

Figure 1B:
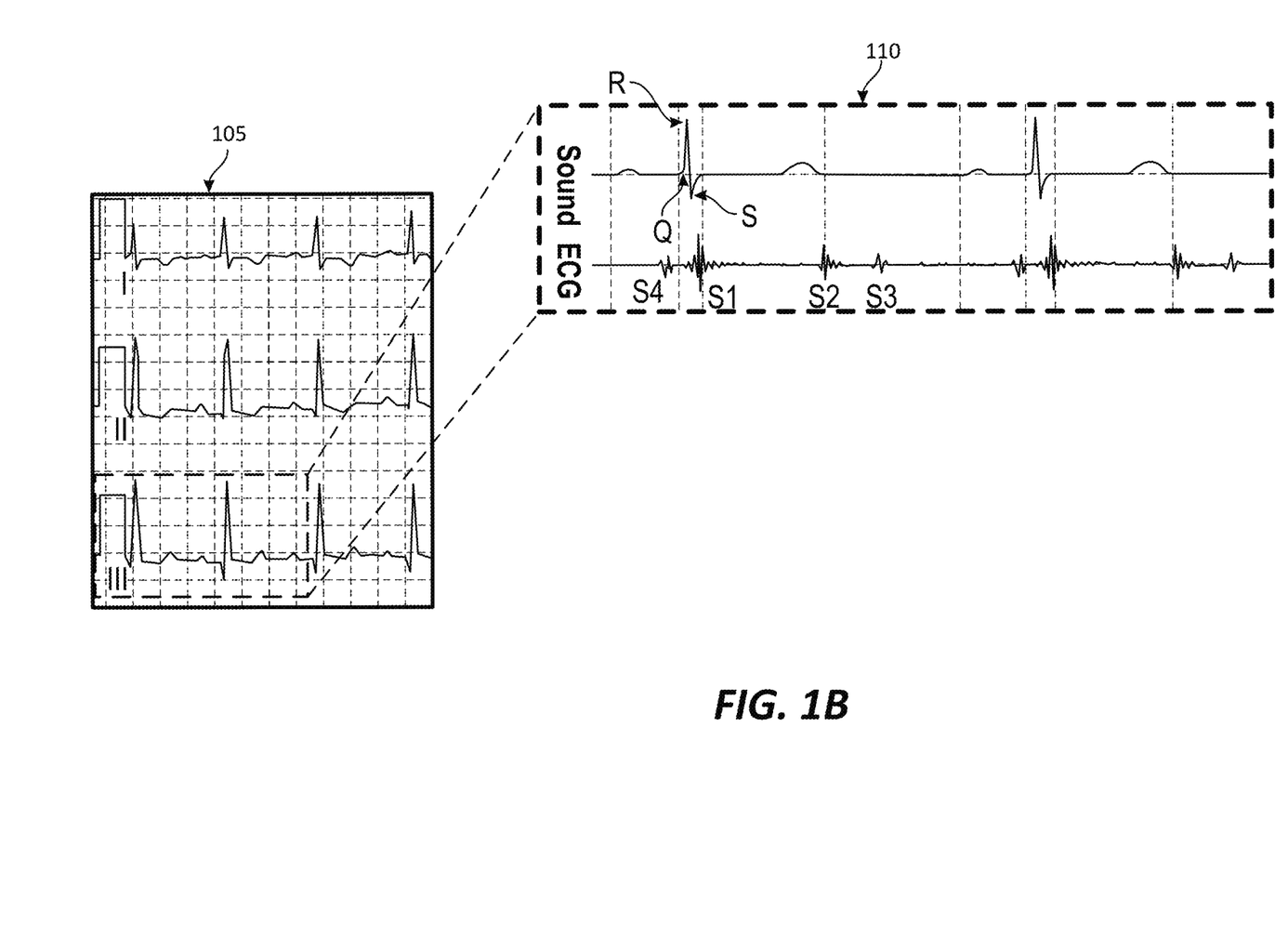
FIG. 1B is a diagram illustrating electrocardiogram (ECG) waveforms, in accordance with some embodiments of the present disclosure.

As noted above, ECG waveforms are generated from measuring multiple leads (each lead formed by a different electrode pair), and the ECG waveform obtained from each different electrode pair/lead may be different/unique (e.g., may have different morphologies/amplitudes). FIG. 1B illustrates a view 105 of an ECG waveform detected by each of 3 leads (I, II, and III) when a 3-lead ECG is taken as well as an exploded view 110 of the ECG waveform measured by lead III. The exploded view 110 may illustrate the QRS complex with the heart sounds S1-S4 displayed below to illustrate the location/timing of the heart sounds S1-S4 relative to the QRS complex. As shown, the amplitudes and morphologies of the ECG waveform taken from leads I-III are all different, with the ECG waveform measured by lead III having the largest amplitude and the ECG waveform measured by lead I having the smallest amplitude. The characteristics of the ECG waveform measured by each lead may also change depending on the location on the person's body where the electrodes of the ECG monitoring device are placed. Stated differently, the ECG waveform measured at each lead may change (e.g., change amplitude and morphology) as the ECG monitoring device moves about the body of the person.

Embodiments of the present disclosure provide an assistive technology to allow anyone to determine a location on the body of a patient where heart sounds may be optimally heard (referred to herein as the optimal location). For the patient, the optimal location may initially be determined using with the help of a physician or may be determined using a clinically validated algorithm and upon determining the optimal location, an ECG may be measured at the optimal location. The ECG data corresponding to the optimal location may be stored in the memory of an auscultation device comprising an acoustic sensor, a set of electrodes and a processing device in addition to the memory. Subsequently, when a person (e.g., physician) wishes to listen to the heart sounds of the patient, the physician may place the auscultation device at a first location on the patient. The auscultation device may perform an ECG and compare the ECG data at the first location to the ECG data at the optimal location to determine and provide feedback to the physician regarding a direction in which the auscultation device should be moved in order to reach the optimal location. The auscultation device may perform this process periodically (e.g., at intervals) to continually guide the physician until the optimal location has been reached. Although described with respect to a physician attempting to perform auscultation on a patient, the embodiments described herein may be used by any person wishing to perform auscultation on another person.

Figure 2:
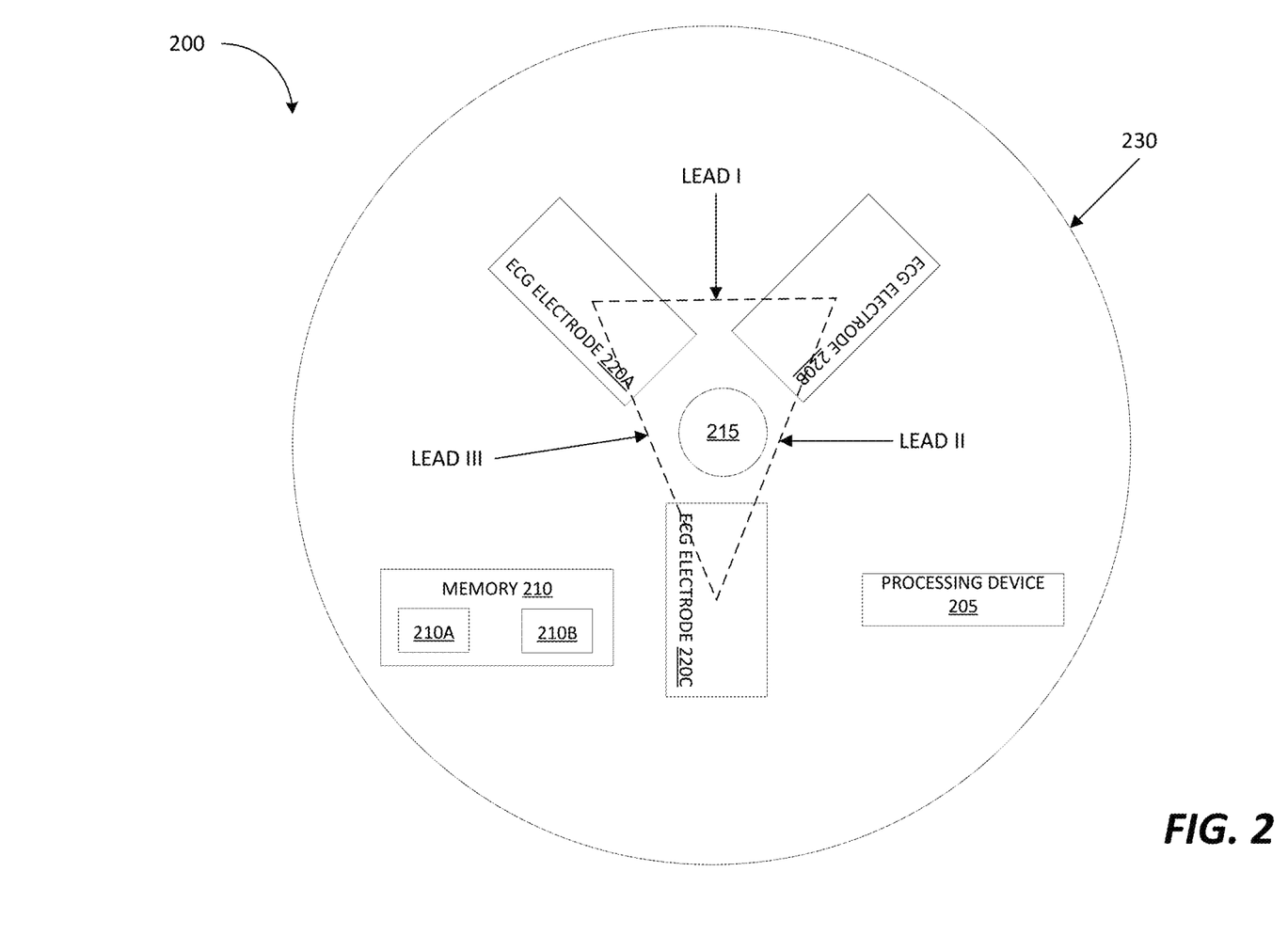
FIG. 2 is a diagram illustrating an auscultation device, in accordance with some embodiments of the present disclosure.

FIG. 2 illustrates an auscultation device 200 for determining/providing guidance to the optimal location on the body of the patient for performing auscultation, in accordance with some embodiments of the present disclosure. The auscultation device 200 may comprise a processing device 205, a memory 210, an auscultation sensor 215, and a set of electrodes 220A-220C. The processing device 205, memory 210, auscultation sensor 215, and the set of electrodes 220A-220C may be integrated into a housing 230. The auscultation sensor 215 may be any appropriate transducer for listening to heart sounds such as e.g., an electronic stethoscope. Although illustrated with three electrodes 220 for ease of illustration and description, embodiments of the present disclosure are not limited in this way and any appropriate number of electrodes (forming any appropriate number of leads) may be utilized. FIG. 2 illustrates the 3 leads I, II, and II formed by the electrodes 220, where leads I, II, and III correspond to the electrical signal measured between electrodes 220A and 220B, 220B and 220C, and 220C and 220A respectively when taking an ECG. The memory 210 may include a location determination module 210A which may be executed by the processing device 120 in order to perform the methods and techniques described herein. Although illustrated with 3 electrodes to perform a 3-lead ECG, embodiments of the present disclosure are not limited in this way and the auscultation device 200 may have any appropriate number of electrodes forming any appropriate number of leads.

The memory 210 may further include a target ECG data store 210B, where ECG data (e.g., waveforms from each different lead) corresponding to an ECG taken at an optimal location on the body of the patient for hearing heart and respiratory sounds (referred to herein as target ECG data) may be stored. The target ECG data store 210B may store target ECG data for a variety of patients. The optimal location for the patient may be determined prior to the patient visit (e.g., during an initial consultation) with the help of a physician or may be determined using a clinically validated algorithm (e.g., an algorithm which uses the ECG morphology and basic anatomical information as inputs to determine the optimal location). Upon determining the optimal location, an ECG may be measured at the optimal location (e.g., using electrodes 220 of the auscultation device 200) to obtain the target ECG data for the patient. The optimal location (e.g., the coordinates thereof) may be correlated with the target ECG data and the target ECG data may be stored in the target ECG data store 210B along with the optimal location. As discussed in further detail herein, the target ECG data may include target ECG parameters that can be used by the auscultation device 200 to assist a physician attempting to listen to heart sounds of the patient in locating the optimal location to do so.

In some embodiments, the target ECG parameters may comprise a ratio of the amplitude and morphology values among the ECG waveforms detected by each of the leads I-III when the ECG is taken at the optimal location. It should be noted that certain the target ECG parameters may comprise a ratio of the amplitude and morphology values of any appropriate wave(s)/complex(s) of the ECG waveforms detected by each of the leads I-III when the ECG is taken at the optimal location. For example, the target ECG parameters may comprise a ratio of the amplitude and morphology values of the QRS complex of the ECG waveforms detected by each of the leads I-III when the ECG is taken at the optimal location.

Upon the auscultation device 200 being placed on the body of the patient, the processing device 205 may take an ECG of the patient using electrodes 220A-220C as described herein and measure an ECG waveform at each lead I-III. As discussed herein, although the leads I-III may analyze the same electrical events, each one may do so from a different angle. As a result, there may be differences (e.g., in amplitude and morphology) in the ECG waveform detected by each lead I-III. The processing device 205 may calculate ECG parameters at the current location based on these differences. In some embodiments, the ECG parameters at the current location may comprise a ratio of the amplitude and morphology values among the ECG waveforms (e.g., the QRS complex thereof) detected by each of the leads I-III when the ECG is taken at the current location. As discussed in further detail herein, the processing device 205 may compare the ECG parameters at the current location to the target ECG parameters for the patient in order to provide directional guidance that will assist the physician attempting to listen to the heart sounds of the patient in finding the optimal location. As the position of the auscultation device 200 on the body of the patient changes (e.g., the physician moves it around based on the directional guidance), the ECG waveform measured by each lead I-III may change. For example, there may be changes to the amplitudes and morphologies of the waveform (e.g., the QRS complex thereof) detected at each lead I-III as the auscultation device 200 moves about the patient's body. Thus, as the auscultation device 200 moves about the patient's body, the processing device 205 may continuously (e.g., at intervals) take an ECG, determine ECG parameters at the current location, and compare them to the target ECG parameters in order to continually provide updated guidance to the physician until they have reached the optimal location. As discussed herein, the amplitude and morphology values of the ECG waveform measured by each lead I-III may refer to the amplitude and morphology values of one particular wave or complex (e.g., the QRS complex) of the ECG waveforms measured by each lead I-III.

Figure 3A:
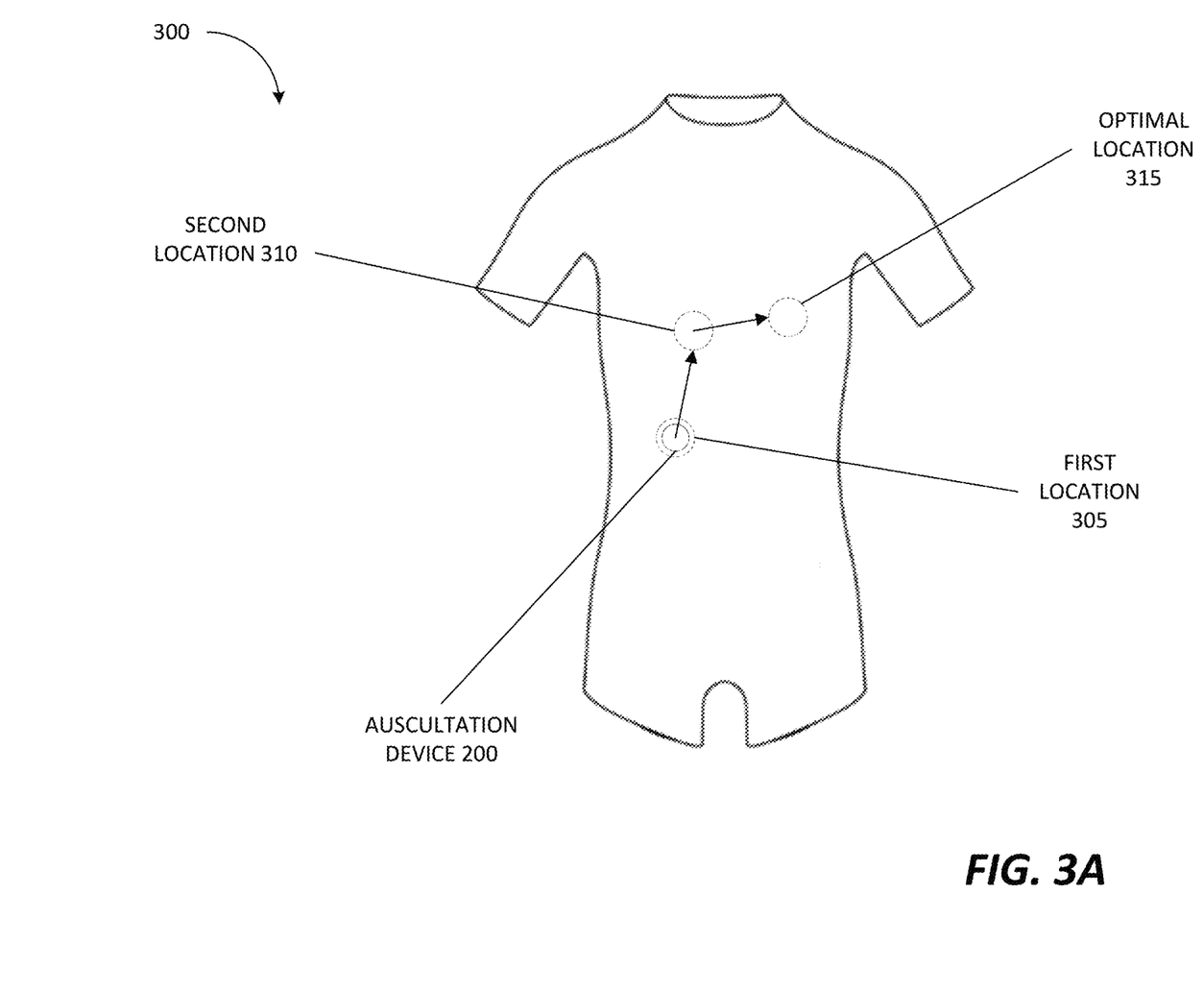
FIG. 3A is a diagram illustrating the auscultation device of FIG. 2 determining the optimal location on a person for performing auscultation, in accordance with some embodiments of the present disclosure.

FIG. 3A illustrates the process of the auscultation device 200 guiding a physician attempting to listen to the heart sounds of the patient to the optimal location 315. The physician may place the auscultation device 200 at a first location 305 on the patient where the processing device 205 may take an ECG of the patient and determine a set of ECG parameters for the first location 305. Because the ECG waveform measured by each lead I-III has different amplitude and morphology values, in some embodiments the set of ECG parameters for the first location 305 may comprise a ratio of the amplitude and morphology values among the ECG waveforms detected at each of the 3 leads I-III when the ECG is taken at the first location 305. The processing device 205 may compare the set of ECG parameters for the first location 305 (e.g., the current ECG parameters) with the target ECG parameters (comprising the ratio of the amplitude and morphology values among the ECG waveforms detected by each of the leads I-III when the ECG is taken at the optimal location 315) stored in the target ECG data store 210B to determine a direction in which the auscultation device 200 should be moved in order to reach the optimal location 315. In some embodiments, the processing device 205 may use any appropriate position determination algorithm (e.g., triangulation, trilateration, or a combination of the 2) to make this determination. More specifically, the processing device 205 may use any appropriate position determination algorithm (e.g., a triangulation algorithm, a trilateration algorithm, or a combination of the two) to determine a direction and a distance in which the auscultation device 200 (e.g., a direction and a distance in which the housing 230) should be moved in order to obtain the target ECG parameters (and thereby reach the optimal location 315) based on the set of ECG parameters at the first location 305 (the ratio of amplitude and morphology values among ECG waveforms detected by leads I-III at the first location 305) and the target ECG parameters (the ratio of amplitude and morphology values among ECG waveforms detected by the leads I-III at the optimal location 315).

The position determination algorithm may utilize a peak value correlation/optimization technique to make this determination, for example. The position determination algorithm may alternatively or additionally rely on machine learning (ML) based methods to make the determination. For example, the algorithm may utilize an ML model trained with training data, to determine when the ratio of the amplitude and morphology values among the ECG waveforms detected by each of the leads I-III all fall within corresponding predetermined thresholds to confirm that the auscultation device 200 has reached the optimal location 315.

Figure 4:
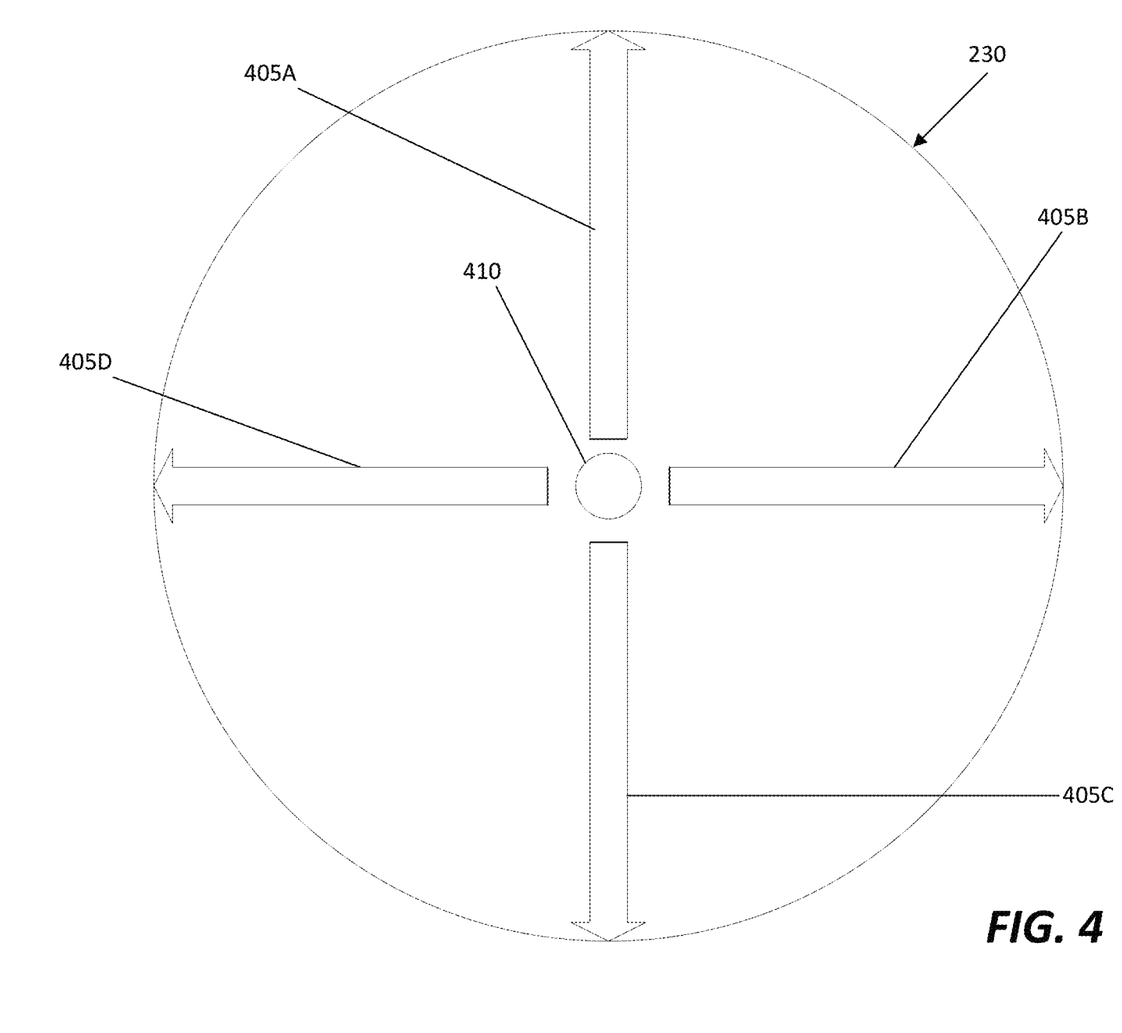
FIG. 4 is a top view of the auscultation device of FIG. 2, in accordance with some embodiments of the present disclosure.

The processing device 205 may provide (via the auscultation device 200 as discussed in further detail herein e.g., with respect to FIG. 4) directional guidance based on the determined direction to the physician. As the physician moves the auscultation device 200 across the patient's body in the determined direction, the processing device 205 may continue (e.g., at intervals) to take an ECG, determine current ECG parameters, and compare the current ECG parameters with the target ECG parameters to provide updated directional guidance. For example, at the first location 305, the physician may receive directional guidance indicating that the auscultation device 200 should be moved northeast. As the physician moves the auscultation device 200 northeast, it may reach a second location 310. As discussed herein, the processing device 205 may take an ECG at the second location 310, determine a set of ECG parameters at the second location 310, and compare the ECG parameters at the second location 310 with the target ECG parameters. More specifically, the processing device 205 may use any appropriate position determination algorithm to determine updated/further refined directional guidance for reaching the optimal location 315 (as discussed above) based on the set of ECG parameters at the second location 310 and the target ECG parameters. In the example of FIG. 3A, the processing device 205 may update the directional guidance at regular intervals, and the second location 310 may correspond to the location the auscultation device 200 is at when the second interval is over.

The processing device 205 may (via the auscultation device 200 as discussed in further detail herein e.g., with respect to FIG. 4) provide directional guidance indicating that it should be moved northeast (but with greater magnitude in the east direction) based on the comparison of the ECG parameters at the second location 310 with the target ECG parameters. Upon reaching the optimal location 315, the auscultation device 200 may provide an indication that the optimal location 315 has been reached (as discussed in further detail herein), and that auscultation may begin. It should be noted that the example of FIG. 3A is illustrative only and the process of taking an ECG, determining ECG parameters at a current location, and using any appropriate position determination algorithm along with the ECG parameters at a current location and the target ECG parameters to determine directional guidance (or updated/further refined directional guidance) for reaching the optimal location 315 may be performed at more or less frequent intervals (e.g., the directional guidance can be provided/updated on a more or less granular scale).

To provide directional guidance, the processing device 205 may utilize directional indicators (e.g., as illustrated in FIG. 4) of the auscultation device 200 to provide an indication of the direction in which the auscultation device 200 should be moved in order to reach the optimal location 315. In some embodiments, the indication may be based on the direction determined based on the use of a position determination algorithm and the set of ECG parameters at a current location and the target ECG parameters, as described above. In other embodiments, the indication may be based on the direction determined based on the use of a position determination algorithm and the set of ECG parameters at a current location and the target ECG parameters, as well as on a direction determined based on maximizing an amplitude of each waveform of the ECG taken at the current location, as discussed in further detail herein.

It has been recognized that the amplitude of the waveform detected by an ECG lead will increase as it is placed closer to the sinus node of the heart. As a result, the optimal location 315 may correspond to the location where the amplitude of the waveform detected by each of the 3 leads I-III is maximized. Thus, in some embodiments, the location determination module 210A may include logic and algorithms to continuously (e.g., at intervals) take an ECG of the patient while the auscultation device 200 moves about the body of the patient, and monitor the amplitude of the ECG waveform detected by each lead I-III as the auscultation device 200 moves about the body of the patient. Based on how the amplitude of each of the ECG waveforms changes as the auscultation device 200 moves, the processing device 205 may determine a direction in which the auscultation device 200 must be moved in order to maximize the amplitude of the ECG waveform detected by each lead I-III. The auscultation device 200 may then provide guidance to the physician to reach the optimal location as discussed in further detail herein.

Figure 3B:
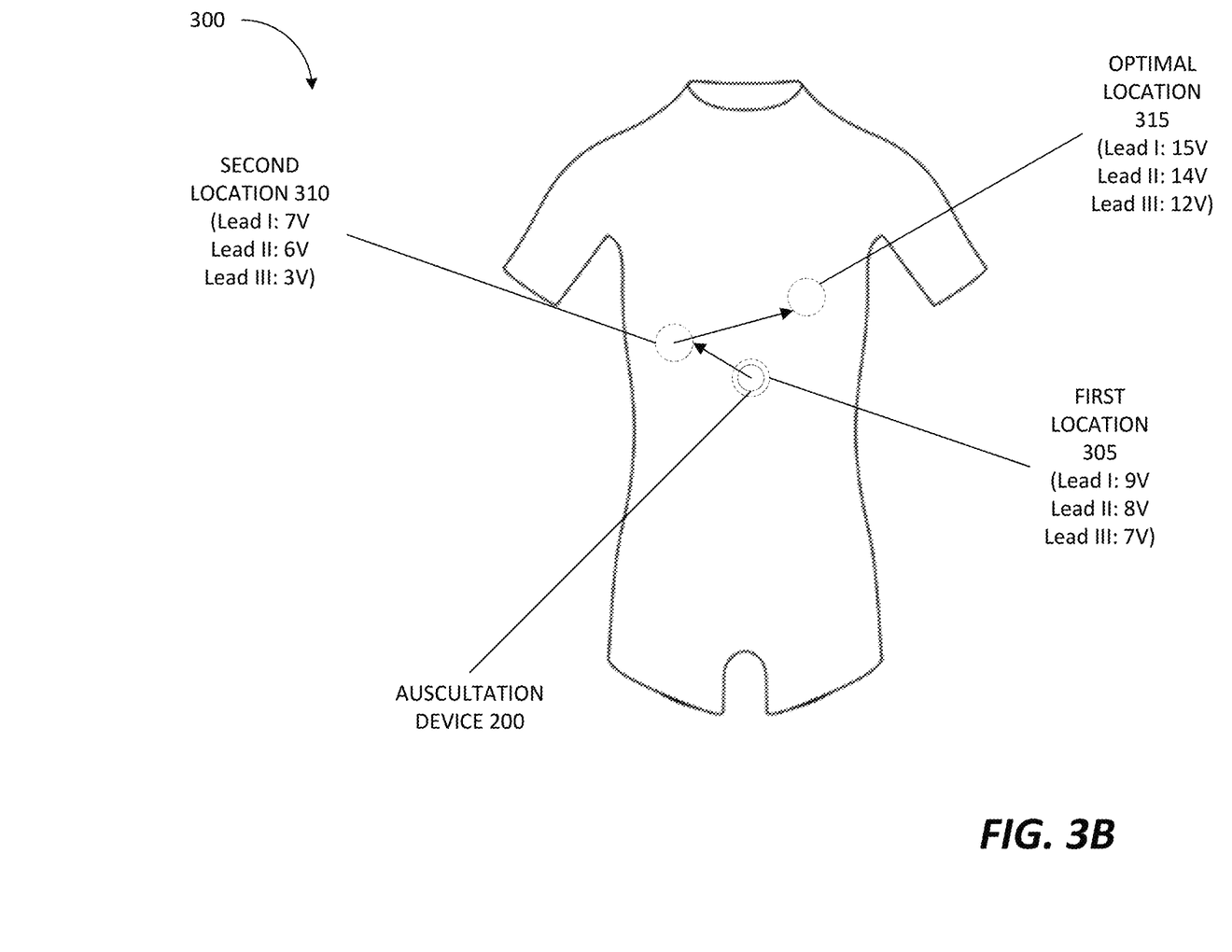
FIG. 3B is a diagram illustrating the auscultation device of FIG. 2 determining the optimal location on a person for performing for auscultation, in accordance with some embodiments of the present disclosure.

FIG. 3B illustrates the process of the auscultation device 200 guiding a physician attempting to listen to the heart sounds of the patient to the optimal location 315 by maximizing the amplitude of the ECG waveform measured by each lead I-III. The physician may start by placing the auscultation device 200 at the first location 305, where the amplitude of the ECG waveform (e.g., the QRS complex thereof) taken by each lead I-III may be 9V, 8V, and 7V respectively (based on an ECG taken by the processing device 205 at the first location 305). The physician may move the auscultation device 200 in a north westerly direction towards the second location 310. At the second location 310, the processing device 205 may take another ECG and determine that the amplitude of the ECG waveform measured by each lead I-III has decreased to 7V, 6V, and 3V respectively. The processing device 205 may provide guidance to the physician indicating that the current direction is incorrect (as discussed in further detail herein) and determine a correct direction based on the current amplitude values of the ECG waveform measured at each of the leads I-III. For example, upon reaching the second location 310, the processing device 205 may take a second ECG and determine that the ECG waveform measured at each lead I-III experienced a decrease in amplitude. More specifically, the processing device 205 may determine that lead III experienced the largest decrease, and based on the decrease experienced by leads I and II as well, the processing device 205 may determine that the auscultation device 200 should be moved in a north easterly direction and provide guidance to the physician to do so as discussed in further detail herein. The processing device 205 may continually perform this process, and continue adjusting the directional guidance provided to the physician until the amplitude of the waveform detected by each of the 3 leads I-III is maximized. As shown in FIG. 3B, the amplitude of an ECG waveform measured at each lead I-III may be 15V, 14V, and 12V respectively upon reaching the optimal location 315. By maximizing the amplitude of the leads I-III, a consistent position for acoustic comparison can be identified. Although described with the processing device 205 performing the second ECG and determining the directional guidance at the second location 310, the processing device 205 may perform this process at any appropriate interval so as to provide continuously updated directional guidance with any appropriate level of granularity.

There may be scenarios in which it is not optimal to treat the location where the amplitude of ECG wavelengths measured at each lead I-III is at a maximum value as the optimal location for auscultation. Thus, in some embodiments, the processing device 205 may provide directional guidance based on a combination of the amplitude maximization and ECG parameter comparison techniques described above.

FIG. 4 illustrates a top view of the auscultation device 200, showing how the processing device 205 (via the auscultation device 200) may provide directional guidance in accordance with some embodiments of the present disclosure. As can be seen, the auscultation device 200 may comprise 4 directional indicators 405A-405D mounted on the housing 230. Each directional indicator 405 may be comprised of light emitting diodes or other appropriate light emitting devices and may be communicatively coupled to the processing device 205. Upon determining directional guidance to be provided to the physician (as discussed in further detail herein), the processing device 205 may illuminate one or more directional indicators 405 corresponding to the direction indicated by the directional guidance. For example, if the processing device 205 determines that the auscultation device 200 should be moved north, it may illuminate the north directional indicator 405A. If the processing device 205 determines that the auscultation device 200 should be moved northeast, then both the north directional indicator 405A and the east directional indicator 405B may be illuminated. In some embodiments, if the processing device 205 determines that the auscultation device 200 should be moved in multiple directions with different magnitudes, it may partially illuminate a directional indicator 405 corresponding to the direction with a lower magnitude and more fully illuminate a directional indicator 405 corresponding to a direction with a higher magnitude. For example, if the processing device 205 determines that the auscultation device 200 should be moved northeast, but with greater magnitude in the north direction and lesser magnitude in the east direction, it may illuminate directional indicator 405A fully and only partially illuminate directional indicator 405B (e.g., directional indicator 405B may be dimmer or less bright than directional indicator 405A). In another example, if the processing device 205 determines that the auscultation device 200 should be moved northeast, but with greater magnitude in the east direction and lesser magnitude in the north direction, it may illuminate a larger number of LEDs within the directional indicator 405A and illuminate a correspondingly smaller number of LEDs in the directional indicator 405B to indicate this. The directional indicators 405 may comprise any appropriate shape such as e.g., an arrow (as illustrated in FIG. 4), a triangle, a straight line, or any other appropriate shape.

If the processing device 205 needs to indicate that the physician is currently moving the auscultation device 200 in the wrong direction, it may illuminate a directional indicator 405 corresponding to the current direction of movement with a particular color. For example, when a directional indicator 405 corresponding to the current direction of movement is illuminated red, this may indicate that the direction is incorrect (i.e., the auscultation device 200 is being moved away from the optimal location), while a directional indicator 405 illuminated green may indicate the direction in which the auscultation device 200 should be moved in order to reach the optimal location.

In some embodiments, the auscultation device 200 may include a target location indicator 410 which may also be comprised of LEDs or any other appropriate light emitting device, and may be illuminated by the processing device 205 when the processing device 205 determines that the auscultation device 200 is at the optimal location.

Figure 5:
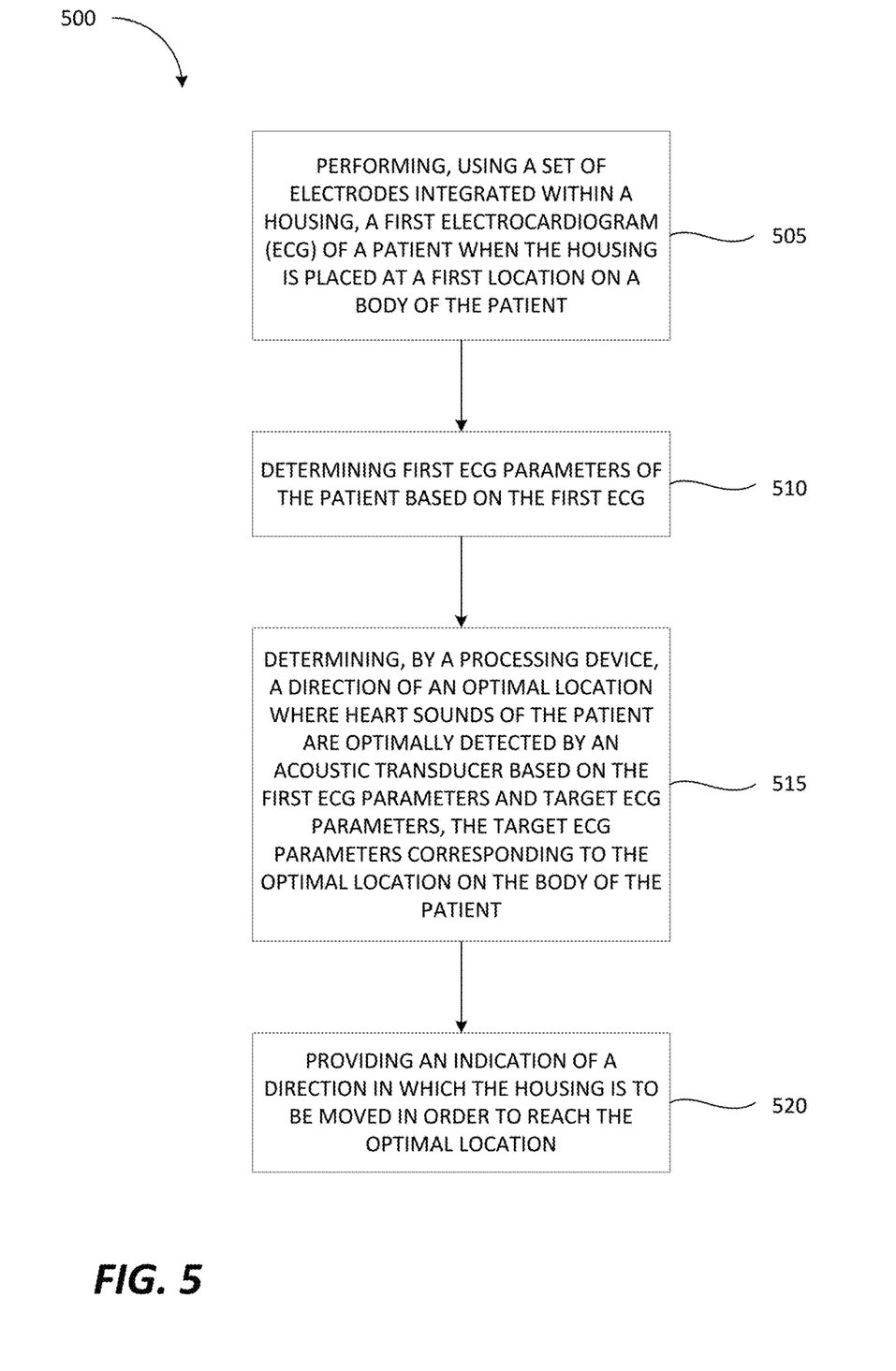
FIG. 5 is a flow diagram of a method for determining the optimal location on the body of a person for performing auscultation, in accordance with some embodiments of the present disclosure.

FIG. 5 is a flow diagram of a method 500 for determining/providing guidance to the optimal location on a person's body to perform auscultation, in accordance with some embodiments of the present disclosure. Method 500 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the method 500 may be performed by auscultation device 200 (e.g., via processing device 205) illustrated in FIG. 2.

Referring simultaneously to FIG. 3A, a physician may place the auscultation device 200 at a first location 305 on the patient where at block 505 the processing device 205 may take an ECG of the patient and determine, at block 510, a set of ECG parameters for the first location 305. Because the ECG waveform measured by each lead I-III has different amplitude and morphology values, in some embodiments the set of ECG parameters for the first location 305 may comprise a ratio of the amplitude and morphology values among the ECG waveforms detected at each of the 3 leads I-III when the ECG is taken at the first location 305. The processing device 205 may compare the set of ECG parameters for the first location 305 (e.g., the current ECG parameters) with the target ECG parameters (comprising the ratio of the amplitude and morphology values among the ECG waveforms detected by each of the leads I-III when the ECG is taken at the optimal location 315) stored in the target ECG data store 210B to determine a direction in which the auscultation device 200 should be moved in order to reach the optimal location 315. In some embodiments, the processing device 205 may use any appropriate position determination algorithm (e.g., triangulation, trilateration, or a combination of the 2) to make this determination. More specifically, at block 515, the processing device 205 may use any appropriate position determination algorithm (e.g., a triangulation algorithm, a trilateration algorithm, or a combination of the two) to determine a direction and a distance in which the auscultation device 200 (e.g., a direction and a distance in which the housing 230) should be moved in order to obtain the target ECG parameters (and thereby reach the optimal location 315) based on the set of ECG parameters at the first location 305 (the ratio of amplitude and morphology values among ECG waveforms detected by leads I-III at the first location 305) and the target ECG parameters (the ratio of amplitude and morphology values among ECG waveforms detected by the leads I-III at the optimal location 315).

At block 520, the processing device may utilize the directional indicators 405 of the auscultation device 200 to provide an indication of the direction in which the auscultation device 200 (e.g., the housing 230 thereof) should be moved in order to reach the optimal location 315. In some embodiments, the indication may be based on the direction determined based on the use of a position determination algorithm and the set of ECG parameters at the current location and the target ECG parameters. In other embodiments, the indication may be based on the direction determined based on the use of a position determination algorithm and the set of ECG parameters at the current location and the target ECG parameters, as well as on a direction determined based on maximizing an amplitude of each waveform of the ECG taken at the current location, as discussed herein (e.g., with respect to FIG. 6).

Figure 6:
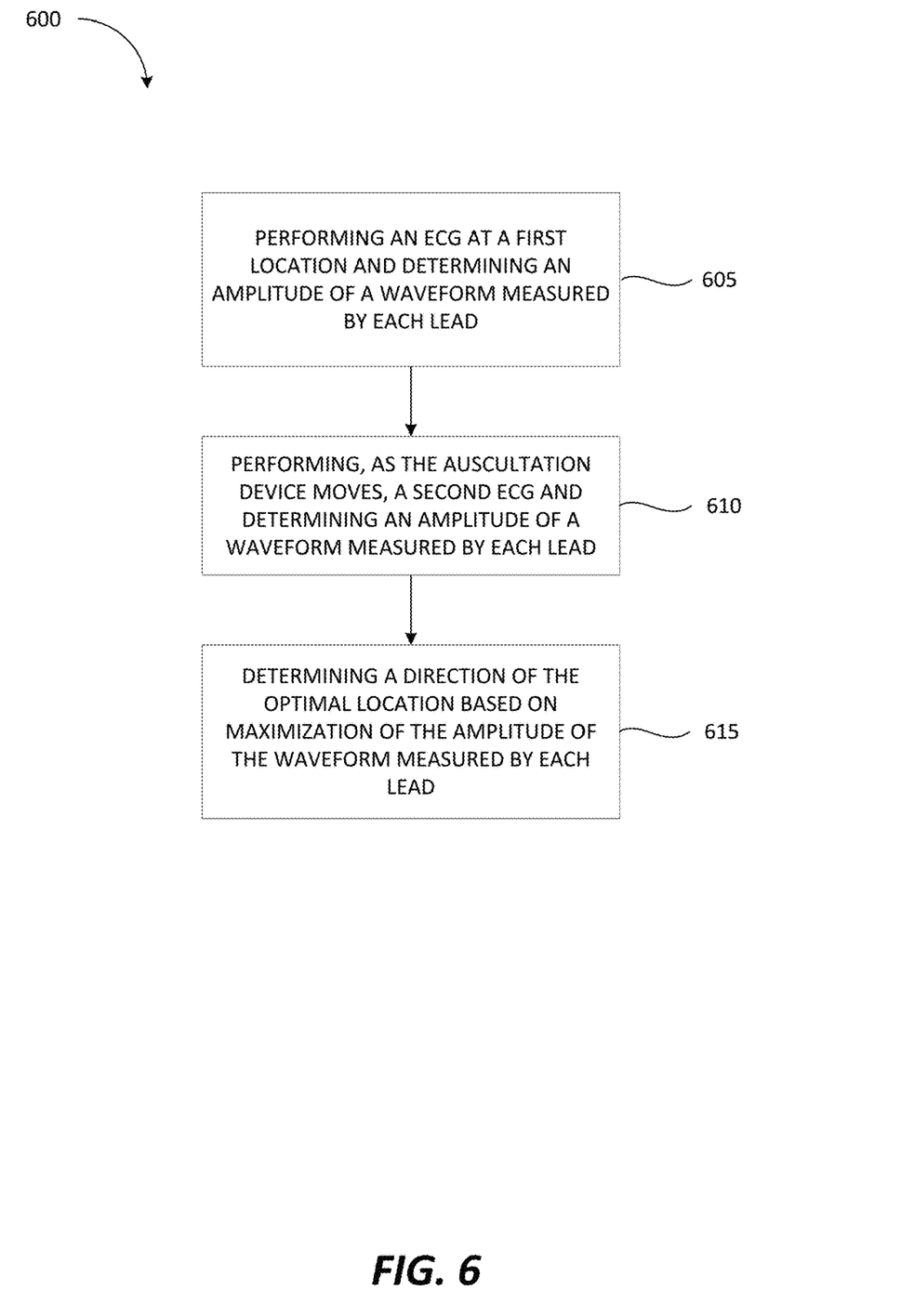
FIG. 6 is a flow diagram of a method for determining the optimal location on the body of a person for performing auscultation based on amplitude maximization, in accordance with some embodiments of the present disclosure.

FIG. 6 is a flow diagram of a method 600 for determining/providing guidance to the optimal location on a person's body to perform auscultation based on amplitude maximization, in accordance with some embodiments of the present disclosure. Method 600 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the method 600 may be performed by auscultation device 200 (e.g., via processing device 205) illustrated in FIG. 2.

Referring simultaneously to FIG. 3B, the physician may start by placing the auscultation device 200 at the first location 305, where at block 605, the processing device 205 may perform an ECG and determine the amplitude of the ECG waveform (e.g., the QRS complex thereof) taken by each lead I-III as 9V, 8V, and 7V respectively. The physician may move the auscultation device 200 in a north westerly direction towards the second location 310. At the second location 310, the processing device 205 at block 610 may take another ECG and determine that the amplitude of the ECG waveform measured by each lead I-III has decreased to 7V, 6V, and 3V respectively. The processing device 205 may provide guidance to the physician indicating that the current direction is incorrect (as discussed in further detail herein) and determine a correct direction based on the current amplitude values of the ECG waveform measured at each of the leads I-III. For example, upon reaching the second location 310, the processing device 205 may take a second ECG and determine that the ECG waveform measured at each lead I-III experienced a decrease in amplitude. More specifically, the processing device 205 may determine that lead III experienced the largest decrease, and based on the decrease experienced by leads I and II as well, the processing device 205 may determine that the auscultation device 200 should be moved in a north easterly direction and provide guidance to the physician to do so as discussed in further detail herein. At block 615, the processing device 205 may continually perform this process, and continue adjusting the directional guidance provided to the physician until the amplitude of the waveform detected by each of the 3 leads I-III is maximized. As shown in FIG. 3B, the amplitude of an ECG waveform measured at each lead I-III may be 15V, 14V, and 12V respectively upon reaching the optimal location 315. By maximizing the amplitude of the leads I-III, a consistent position for acoustic comparison can be identified. Although described with the processing device 205 performing the second ECG and determining the directional guidance at the second location 310, the processing device 205 may perform this process at any appropriate interval so as to provide continuously updated directional guidance with any appropriate level of granularity.

There may be scenarios in which it is not optimal to treat the location where the amplitude of ECG wavelengths measured at each lead I-III is at a maximum value as the optimal location for auscultation. Thus, in some embodiments, the processing device 205 may provide directional guidance based on a combination of the amplitude maximization and ECG parameter comparison techniques described above.

Figure 7:
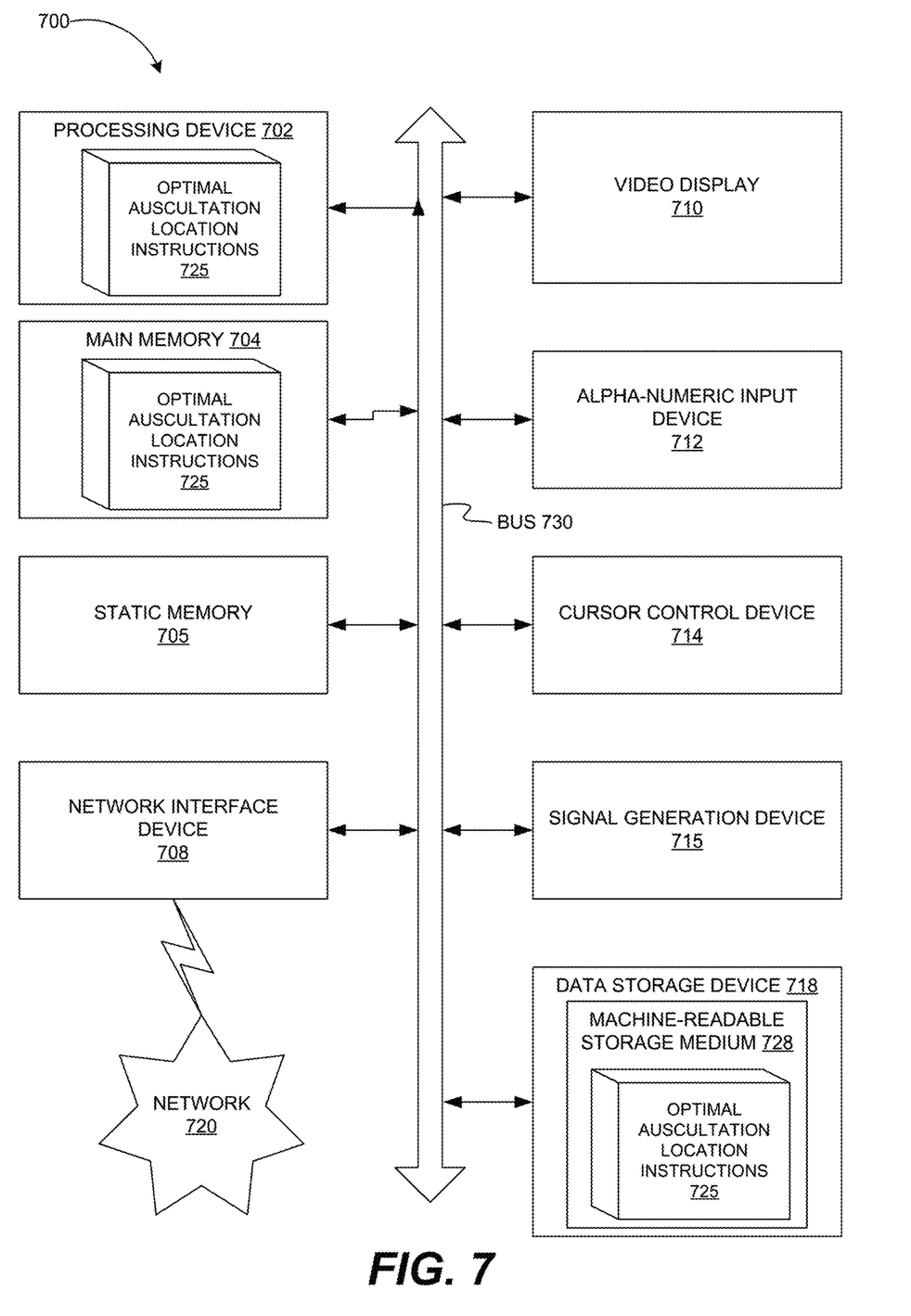
FIG. 7 is a block diagram of an example computing device that may perform one or more of the operations described herein, in accordance with some embodiments of the present disclosure.

FIG. 7 illustrates a diagrammatic representation of a machine in the example form of a computer system 700 within which a set of instructions, for causing the machine to perform any one or more of the methodologies discussed herein for providing guidance to the optimal location on a person to perform auscultation.

In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, a switch or bridge, a hub, an access point, a network access control device, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In one embodiment, computer system 700 may be representative of a server.

The exemplary computer system 700 includes a processing device 702, a main memory 704 (e.g., read-only memory (ROM), flash memory, dynamic random access memory (DRAM), a static memory 706 (e.g., flash memory, static random access memory (SRAM), etc.), and a data storage device 718, which communicate with each other via a bus 730. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Computing device 700 may further include a network interface device 708 which may communicate with a network 720. The computing device 700 also may include a video display unit 710 (e.g., a liquid crystal display (LCD) or a cathode ray tube (CRT)), an alphanumeric input device 712 (e.g., a keyboard), a cursor control device 714 (e.g., a mouse) and an acoustic signal generation device 716 (e.g., a speaker). In one embodiment, video display unit 710, alphanumeric input device 712, and cursor control device 714 may be combined into a single component or device (e.g., an LCD touch screen).

Processing device 702 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. The processing device 702 is configured to execute optimal auscultation location instructions 725, for performing the operations and steps discussed herein.

The data storage device 715 may include a machine-readable storage medium 728, on which is stored one or more sets of optimal auscultation location instructions 725 (e.g., software) embodying any one or more of the methodologies of functions described herein. The optimal auscultation location instructions 725 may also reside, completely or at least partially, within the main memory 704 or within the processing device 702 during execution thereof by the computer system 700; the main memory 704 and the processing device 702 also constituting machine-readable storage media. The optimal auscultation location instructions 725 may further be transmitted or received over a network 720 via the network interface device 708.

While the machine-readable storage medium 728 is shown in an exemplary embodiment to be a single medium, the term "machine-readable storage medium" should be taken to include a single medium or multiple media (e.g., a centralized or distributed database, or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein. These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into may other different systems or applications. Various presently unforeseen or unanticipated alternatives, modifications, variations, or improvements therein may be subsequently made by those skilled in the art which are also intended to be encompassed by the following claims. The claims may encompass embodiments in hardware, software, or a combination thereof

What is claimed is:

1. An apparatus comprising:
   a housing comprising:
   an acoustic transducer to detect a set of heart sounds when the housing is placed on a body of a patient;
   a set of electrodes to measure cardiac electrical activity of the patient;
   a memory to store target ECG parameters, the target ECG parameters corresponding to an optimal location on the body of the patient where the set of heart sounds are optimally detected by the acoustic transducer; and
   a processing device, operatively coupled to the memory, the processing device to:
   perform, using the set of electrodes, a first electrocardiogram (ECG) of the patient when the housing is placed at a first location on the body of the patient;
   determine first ECG parameters of the patient based on the first ECG;
   determine a direction of the optimal location from the first location based on the first ECG parameters and the target ECG parameters; and
   provide an indication of a direction in which the housing is to be moved in order to reach the optimal location.

2. The apparatus of claim 1, wherein to determine the first ECG parameters of the patient, the processing device is to:
   determine an amplitude and a morphology of each of a set of waveforms measured during the first ECG of the patient, each waveform in the set of waveforms measured by a pair of electrodes within the set of electrodes; and
   determine a first ratio of the amplitude and morphology of each of the set of waveforms.

3. The apparatus of claim 2, wherein the target ECG parameters comprise a target ratio of the amplitude and morphology of each of a set of waveforms measured during an ECG of the patient performed at the optimal location.

4. The apparatus of claim 3, wherein to determine the direction of the optimal location from the first location, the processing device is to:
   use a position determination algorithm to determine the direction of the optimal location from the first location based on the first ECG parameters and the target ECG parameters.

5. The apparatus of claim 1, wherein the processing device is further to:
   perform, using the set of electrodes, a second ECG of the patient when the housing is moved to a second location on the body of the patient;
   determine second ECG parameters of the patient based on the second ECG;

determine a direction of the optimal location from the second location based on the second ECG parameters and the target ECG parameters; and provide an updated indication of the direction in which the housing is to be moved in order to reach the optimal location.

6. The apparatus of claim 1, further comprising a set of directional indicators, and wherein to provide the indication of the direction in which the housing should be moved, the processing device is to:

utilize one or more directional indicators of the set of direction indicators, the one or more directional indicators corresponding to the direction in which the housing should be moved.

7. The apparatus of claim 1, wherein the processing device is further to:

determine an amplitude of each of a set of waveforms measured during the first ECG of the patient;

determine the direction of the optimal location from the first location based on a maximization of the amplitude of each of the set of waveforms measured during the first ECG of the patient, wherein the processing device provides the indication of the direction in which the housing is to be moved based on the first ECG parameters, the target ECG parameters, and the maximization of the amplitude of each of the set of waveforms measured during the first ECG of the patient.

8. A method comprising:

performing, using a set of electrodes integrated within a housing, a first electrocardiogram (ECG) of a patient when the housing is placed at a first location on a body of the patient;

determining first ECG parameters of the patient based on the first ECG;

determining, by a processing device, a direction of an optimal location where heart sounds of the patient are optimally detected by an acoustic transducer based on the first ECG parameters and target ECG parameters, the target ECG parameters corresponding to the optimal location on the body of the patient; and providing an indication of a direction in which the housing is to be moved in order to reach the optimal location.

9. The method of claim 8, wherein determining the first ECG parameters comprises:

determining an amplitude and a morphology of each of a set of waveforms measured during the first ECG of the patient, each waveform in the set of waveforms measured by a pair of electrodes within the set of electrodes; and determining a first ratio of the amplitude and morphology of each of the set of waveforms.

10. The method of claim 9, wherein the target ECG parameters comprise a target ratio of the amplitude and morphology of each of a set of waveforms measured during an ECG of the patient performed at the optimal location.

11. The method of claim 10, wherein determining the direction of the optimal location comprises:

using a position determination algorithm to determine the direction of the optimal location from the first location based on the first ECG parameters and the target ECG parameters.

12. The method of claim 8, further comprising:

performing, using the set of electrodes, a second ECG of the patient when the housing is moved to a second location on the body of the patient;

determining second ECG parameters of the patient based on the second ECG;

determining a direction of the optimal location from the second location based on the second ECG parameters and the target ECG parameters; and providing an updated indication of the direction in which the housing is to be moved in order to reach the optimal location.

13. The method of claim 8, wherein providing the indication of the direction in which the housing should be moved comprises:

utilizing one or more of a set of directional indicators integrated with the housing to provide the indication of the direction in which the housing should be moved, the one or more directional indicators corresponding to the direction in which the housing should be moved.

14. The method of claim 8, further comprising:

determining an amplitude of each of a set of waveforms measured during the first ECG of the patient; and determining the direction of the optimal location from the first location based on a maximization of the amplitude of each of the set of waveforms measured during the first ECG of the patient, wherein providing the indication of the direction in which the housing is to be moved is based on the first ECG parameters, the target ECG parameters, and the maximization of the amplitude of each of the set of waveforms measured during the first ECG of the patient.

15. A non-transitory computer-readable medium having instructions stored thereon which, when executed by a processing device, cause the processing device to:

perform, using a set of electrodes integrated within a housing, a first electrocardiogram (ECG) of a patient when the housing is placed at a first location on a body of the patient;

determine first ECG parameters of the patient based on the first ECG;

determine a direction of an optimal location where heart sounds of the patient are optimally detected by an acoustic transducer based on the first ECG parameters and target ECG parameters, the target ECG parameters corresponding to the optimal location on the body of the patient; and provide an indication of a direction in which the housing is to be moved in order to reach the optimal location.

16. The non-transitory computer-readable medium of claim 15, wherein to determine the first ECG parameters, the processing device is to:

determine an amplitude and a morphology of each of a set of waveforms measured during the first ECG of the patient, each waveform in the set of waveforms measured by a pair of electrodes within the set of electrodes; and determine a first ratio of the amplitude and morphology of each of the set of waveforms.

17. The non-transitory computer-readable medium of claim 16, wherein the target ECG parameters comprise a target ratio of the amplitude and morphology of each of a set of waveforms measured during an ECG of the patient performed at the optimal location.

18. The non-transitory computer-readable medium of claim 17, wherein to determine the direction of the optimal location, the processing device is to:

use a position determination algorithm to determine the direction of the optimal location from the first location based on the first ECG parameters and the target ECG parameters.

19. The non-transitory computer-readable medium of claim 15, wherein the processing device is further to:
perform, using the set of electrodes, a second ECG of the patient when the housing is moved to a second location on the body of the patient;
determine second ECG parameters of the patient based on the second ECG;
determine a direction of the optimal location from the second location based on the second ECG parameters and the target ECG parameters; and
provide an updated indication of the direction in which the housing is to be moved in order to reach the optimal location.

20. The non-transitory computer-readable medium of claim 15, wherein to provide the indication of the direction in which the housing should be moved, the processing device is to:
utilize one or more of a set of directional indicators integrated with the housing to provide the indication of the direction in which the housing should be moved, the one or more directional indicators corresponding to the direction in which the housing should be moved.

\* \* \* \* \*